(12) United States Patent
Taylor et al.

(10) Patent No.: US 11,839,558 B2
(45) Date of Patent: Dec. 12, 2023

(54) MEDICAL DEVICE SUITABLE FOR LOCATION IN A BODY LUMEN

(71) Applicant: Veryan Medical Limited, Oxford (GB)

(72) Inventors: Charles Taylor, Coolham (GB); Kevin Heraty, Castlebar (IE); Liam Mullins, Athlone (IE)

(73) Assignee: Veryan Medical Limited, Oxford (GB)

( * ) Notice: Subject to any disclaimer, the term of this patent is extended or adjusted under 35 U.S.C. 154(b) by 887 days.

(21) Appl. No.: 16/594,331

(22) Filed: Oct. 7, 2019

(65) Prior Publication Data

US 2020/0030122 A1 Jan. 30, 2020

Related U.S. Application Data

(63) Continuation of application No. 12/463,039, filed on May 8, 2009, now Pat. No. 10,456,276.

(51) Int. Cl.
*A61F 2/82* (2013.01)
*A61F 2/94* (2013.01)
(Continued)

(52) U.S. Cl.
CPC .......... *A61F 2/82* (2013.01); *A61F 2/89* (2013.01); *A61F 2/94* (2013.01); *A61F 2002/30199* (2013.01); *A61F 2002/825* (2013.01); *A61F 2002/828* (2013.01); *A61F 2002/91508* (2013.01); *A61F 2002/91541* (2013.01);
(Continued)

(58) Field of Classification Search
CPC ........... A61F 2/04–2002/077; A61F 2/82–945; A61F 2230/0063; A61F 2230/0091
See application file for complete search history.

(56) References Cited

U.S. PATENT DOCUMENTS

| 5,449,373 A | 9/1995 | Pinchasik et al. |
| 5,938,697 A | 8/1999 | Killion et al. |
(Continued)

FOREIGN PATENT DOCUMENTS

| DE | 10 2005 050 386 A1 | 4/2007 |
| EP | 0 800 801 A1 | 10/1997 |
(Continued)

OTHER PUBLICATIONS

Cheng, Christopher P. (Editor), "Handbook of Vascular Motion", Academic Press, Copyright 2019 Elsevier Inc., 22 miscellaneous pages of 413.
(Continued)

*Primary Examiner* — Rebecca S Preston
(74) *Attorney, Agent, or Firm* — Lippes Mathias LLP

(57) ABSTRACT

A stent suitable for deployment in a blood vessel to support at least part of an internal wall of the blood vessel comprises a plurality of longitudinally spaced-apart annular elements, and a plurality of connecting elements to connect adjacent annular elements. Each connecting element is circumferentially offset from the previous connecting element. Upon application of a load to the stent, the stent moves from an unloaded configuration to a loaded configuration. In the unloaded configuration the longitudinal axis of the stent is straight, and the stent is cylindrically shaped. In the loaded configuration the longitudinal axis of the stent is curved in three-dimensional space, and the stent is helically shaped.

27 Claims, 5 Drawing Sheets

(51) Int. Cl.
*A61F 2/89* (2013.01)
*A61F 2/30* (2006.01)
*A61F 2/915* (2013.01)

(52) U.S. Cl.
CPC ............... *A61F 2220/0058* (2013.01); *A61F 2230/0063* (2013.01); *A61F 2230/0091* (2013.01); *A61F 2250/0036* (2013.01); *A61F 2250/0037* (2013.01)

(56) References Cited

U.S. PATENT DOCUMENTS

| | | |
|---|---|---|
| 6,001,123 A | 12/1999 | Lau |
| 6,270,524 B1 | 8/2001 | Kim |
| 6,896,697 B1 | 5/2005 | Yip et al. |
| 7,018,401 B1 | 3/2006 | Hyodoh et al. |
| 7,625,400 B2 | 12/2009 | Bowe et al. |
| 7,731,747 B2 | 6/2010 | Kaplan et al. |
| 8,226,704 B2 | 7/2012 | Caro et al. |
| 8,236,043 B2 | 8/2012 | Caro et al. |
| 8,425,585 B2 | 4/2013 | Melsheimer et al. |
| 8,882,826 B2 | 11/2014 | Ta et al. |
| 2001/0025130 A1 | 9/2001 | Tomonto |
| 2002/0179166 A1 | 12/2002 | Houston et al. |
| 2002/0183853 A1 | 12/2002 | Mitchell et al. |
| 2003/0088305 A1 | 5/2003 | Van Schie et al. |
| 2003/0187497 A1 | 10/2003 | Boylan et al. |
| 2004/0087997 A1 | 5/2004 | Brenneman |
| 2004/0117004 A1 | 6/2004 | Osborne et al. |
| 2005/0096733 A1 | 5/2005 | Kovneristy et al. |
| 2006/0030926 A1 | 2/2006 | Berra |
| 2006/0064120 A1 | 3/2006 | Levine et al. |
| 2006/0217795 A1 | 9/2006 | Besselink et al. |
| 2006/0265051 A1 | 11/2006 | Caro et al. |
| 2007/0055299 A1 | 3/2007 | Ishimaru et al. |
| 2007/0191927 A1 | 8/2007 | Bowe et al. |
| 2008/0086854 A1 | 4/2008 | Boyd et al. |
| 2008/0167707 A1* | 7/2008 | Marrey ............... A61F 2/91 623/1.16 |
| 2008/0195189 A1 | 8/2008 | Asgari |
| 2008/0262599 A1 | 10/2008 | Caro et al. |
| 2008/0306440 A1 | 12/2008 | Hirszowicz et al. |
| 2009/0149945 A1 | 6/2009 | Pike |
| 2009/0234431 A1 | 9/2009 | Weinberger et al. |
| 2010/0094402 A1* | 4/2010 | Heraty ............... A61F 2/82 623/1.34 |
| 2010/0094403 A1 | 4/2010 | Heraty et al. |
| 2010/0286759 A1 | 11/2010 | Taylor et al. |
| 2012/0283819 A1 | 11/2012 | Taylor et al. |
| 2012/0330402 A1 | 12/2012 | Vad et al. |

FOREIGN PATENT DOCUMENTS

| | | |
|---|---|---|
| EP | 0 951 877 | 10/1999 |
| EP | 1 279 382 A1 | 1/2003 |
| EP | 2 174 623 A1 | 4/2010 |
| EP | 2 174 624 A1 | 4/2010 |
| GB | 2 418 362 A | 3/2006 |
| GB | 2 425 485 | 11/2006 |
| JP | H 11-332998 | 12/1999 |
| JP | 2002-535075 A | 10/2002 |
| JP | 2005-013302 | 1/2005 |
| JP | 2007-144108 A | 6/2007 |
| JP | 2008-513171 | 5/2008 |
| JP | 4064724 B2 | 3/2019 |
| WO | WO 98/20810 | 5/1998 |
| WO | WO 00/44308 | 8/2000 |
| WO | WO 03/059199 A1 | 7/2003 |
| WO | WO 2006/032902 | 3/2006 |
| WO | WO 2007/053791 A1 | 5/2007 |
| WO | WO 2007/062661 A1 | 6/2007 |
| WO | WO 2008/117256 A2 | 10/2008 |
| WO | WO 2008/125842 A1 | 10/2008 |
| WO | WO 2010/128311 A1 | 11/2010 |

OTHER PUBLICATIONS

International Search Report of corresponding International Application No. PCT/GB2010/000944 dated Aug. 25, 2010 (English Text).

European Search Report corresponding to EP 09 25 1283, dated Oct. 22, 2009 (English Text).

* cited by examiner

MEDICAL DEVICE SUITABLE FOR LOCATION IN A BODY LUMEN

This application is a continuation application of U.S. patent application Ser. No. 12/463,039 which was filed on May 8, 2009 and is still pending.

BACKGROUND

Introduction

This invention relates to a medical device suitable for location in a body lumen.

Statements of Invention

According to the invention there is provided a medical device suitable for location in a body lumen, upon application of a load to the device the device being movable from an unloaded configuration to a loaded configuration, in the loaded configuration at least part of the longitudinal axis of the device being curved in three-dimensional space. The three-dimensional curved shape of the device maximises the fracture resistance of the device. In the case of certain types of loading, for example compressive loading, the three-dimensional curved shape of the device may minimise points of stress concentration.

In the loaded configuration at least part of the device may be substantially helically shaped. At least part of the longitudinal axis of the device may be substantially helically shaped. In the loaded configuration at least part of the device may be substantially spiral shaped. In the unloaded configuration at least part of the longitudinal axis of the device may be substantially straight. Preferably in the unloaded configuration at least part of the device is substantially cylindrically shaped. In the unloaded configuration at least part of the longitudinal axis of the device may be curved in a two-dimensional plane.

The device may be configured to move from the unloaded configuration to the loaded configuration upon application of a compressive load to the device.

In one embodiment of the invention the device comprises a plurality of annular elements. Preferably the device comprises a plurality of primary connecting elements to connect adjacent annular elements. Ideally the device comprises a first primary connecting element to connect a first annular element to a second annular element, and a second primary connecting element to connect the second annular element to a third annular element, the first primary connecting element being circumferentially offset from the second primary connecting element. This arrangement facilitates the three-dimensional curved shape of the device in the loaded configuration. Most preferably in the unloaded configuration at least part of the longitudinal axis of the aggregation of the plurality of primary connecting elements is curved in three-dimensional space. Similarly this arrangement facilitates the three-dimensional curved shape of the device in the loaded configuration.

In one example the first and second primary connecting elements extend generally perpendicularly to the circumferential direction, and join the second annular element at respective locations which are circumferentially offset. In other embodiments, the first and second primary connecting elements extend in a direction with a component in the circumferential direction and a component in the longitudinal direction. This arrangement can achieve the circumferential offset in an example where the first and second primary connecting elements join the second annular element at respective locations which are not circumferentially offset. In another example of the arrangement in which the first and second primary connecting elements extend in a direction with a component in the circumferential direction and a component in the longitudinal direction, the first and second primary connecting elements join the second annular element at respective locations which are circumferentially offset.

The device may comprise a plurality of secondary connecting elements to connect adjacent annular elements. Preferably the device comprises a first secondary connecting element to connect a first annular element to a second annular element, and a second secondary connecting element to connect the second annular element to a third annular element, the first secondary connecting element being circumferentially offset from the second secondary connecting element. This arrangement facilitates the three-dimensional curved shape of the device in the loaded configuration. Ideally in the unloaded configuration at least part of the longitudinal axis of the aggregation of the plurality of secondary connecting elements is curved in three-dimensional space. Similarly this arrangement facilitates the three-dimensional curved shape of the device in the loaded configuration.

The circumferential dimension of the primary connecting element may be greater than the circumferential dimension of the secondary connecting element. The longitudinal dimension of the primary connecting element may be greater than the longitudinal dimension of the secondary connecting element. The radial dimension of the primary connecting element may be greater than the radial dimension of the secondary connecting element. The stiffness of the primary connecting element may be less than the stiffness of the secondary connecting element.

In one case the longitudinal dimension of the annular element varies around the circumference of the annular element. Preferably the device comprises a first annular element and a second annular element, the point on the circumference of the first annular element where the longitudinal dimension is at a maximum being circumferentially offset from the point on the circumference of the second annular element where the longitudinal dimension is at a maximum. This arrangement facilitates the three-dimensional curved shape of the device in the loaded configuration. Ideally in the unloaded configuration at least part of the longitudinal axis of the aggregation of the plurality of points on the circumference of the annular elements where the longitudinal dimension is at a maximum is curved in three-dimensional space. Similarly this arrangement facilitates the three-dimensional curved shape of the device in the loaded configuration.

In one case the device comprises less than six connecting elements to connect a first annular element to a second annular element. By using a relatively small number of connecting elements, the device is more readily able to move from the unloaded configuration to the loaded configuration with the three-dimensional curved shape. The device may comprise less than four connecting elements to connect a first annular element to a second annular element. The device may comprise a single connecting element to connect a first annular element to a second annular element.

In another case the device is suitable for location in a blood vessel. In the case of some blood vessels, for example the superficial femoral artery, upon application of a load to the blood vessel the blood vessel may curve in three-dimensional space. Because the device located in the blood vessel is curved in three-dimensional space in the loaded configuration, this arrangement enables the device to accommodate the blood vessel deformations in a controlled way. Preferably the device comprises a stent suitable for deployment in a blood vessel. When the stent is deployed in the blood vessel, the stent exerts force on the blood vessel causing at least part of the longitudinal axis of the blood vessel to curve in three-dimensional space. Blood flowing through the three-dimensional curved pail of the blood vessel undergoes a swirling action. The swirling flow of blood has been found to minimise thrombosis and platelet adhesion, and to minimise or prevent coverage of the stent by ingrowth of intima. The flow pattern in the blood vessel including the swirling pattern induced by the non-planar geometry of the blood vessel operates to inhibit the development of vascular diseases such as thrombosis/atherosclerosis and intimal hyperplasia.

BRIEF DESCRIPTION OF THE DRAWINGS

The invention will be more clearly understood from the following description of some embodiments thereof, given by way of example only, with reference to the accompanying drawings, in which.

DETAILED DESCRIPTION

Figure 1:
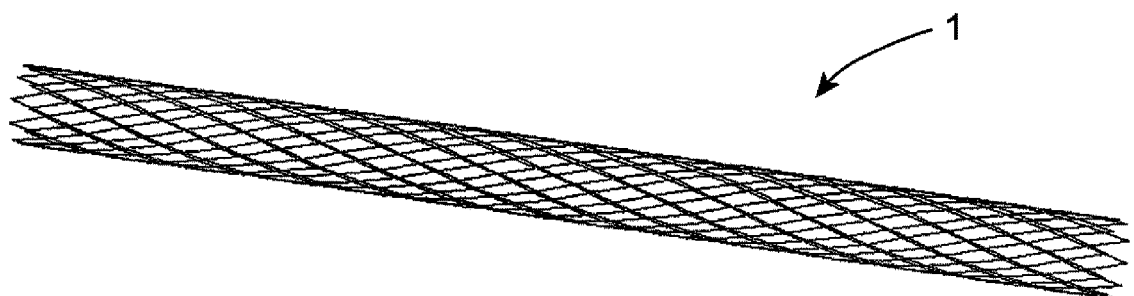
FIG. 1 is an isometric view of a medical device according to the invention in an unloaded configuration.
Figure 2:
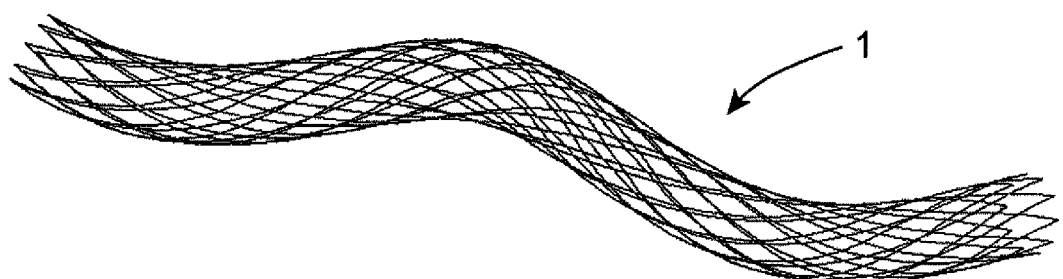
FIG. 2 is an isometric view of the device of FIG. 1 in a loaded configuration.

Referring to the drawings, and initially to FIGS. 1 and 2 thereof, there is illustrated a stent 1 according to the invention suitable for deployment in a blood vessel to support at least part of an internal wall of the blood vessel.

Upon application of a load to the stent 1, such as a compressive load, the stent 1 moves from an unloaded configuration (FIG. 1) to a loaded configuration (FIG. 2). In the unloaded configuration the longitudinal axis of the stent 1 is straight, and the stent 1 is cylindrically shaped. In the loaded configuration the longitudinal axis of the stent 1 is curved in three-dimensional space, and the stent 1 is helically shaped.

FIGS. 1 and 2 illustrate the unloaded and loaded configurations of the stent 1 which is biased to achieve the three dimensional curvature during loading.

It will be appreciated that the stent 1 may have an alternative shape in the loaded configuration, for example a spiral shape.

In use, the stent 1 is collapsed to a delivery configuration and inserted into the blood vessel. The stent 1 is advanced through the blood vessel using a delivery catheter to a deployment site. The stent 1 is caused to expand from the delivery configuration to a deployment configuration at the deployment site. The stent 1 may be a self expanding stent, or alternatively the stent 1 may be expanded using a balloon on the delivery catheter.

The deployed stent 1 in the unloaded configuration is cylindrically shaped with the straight longitudinal axis. Upon application of a load to the stent 1, the stent 1 moves from the unloaded configuration to the loaded configuration. The deployed stent 1 in the loaded configuration is helically shaped with the three-dimensional curved longitudinal axis.

The stent 1 has the straight configuration outside of the blood vessel, and the straight configuration inside the blood vessel before loading. When loaded the stent 1 moves into the three dimensional curvature configuration, such as helical or spiral. The stent 1 is biased to achieve the three dimensional curvature during loading. This controlled change in geometry may be achieved through regional variations in the properties of the stent 1.

The deployment site for the stent 1 may be in the blood vessel in the leg behind the knee which is subject to frequent bending as the patient bends the leg. During bending of the leg, the path of this blood vessel which is known as the superficial femoral artery may shorten, causing its geometry to change from straight into a spiral configuration. This results in the artery having a three dimensional curvature when loaded. The deployed stent 1 in the superficial femoral artery is also subject to this compressive loading. Because the stent 1 is biased into taking up a three dimensional configuration within the artery during loading, the stent 1 accommodates the blood vessel deformations in a controlled way, improving fracture resistance while also improving flow conditions.

When the stent 1 is deployed in the blood vessel, the stent 1 exerts force on the blood vessel causing at least part of the longitudinal axis of the blood vessel to curve in three-dimensional space. In this manner the stent 1 acts to support at least part of the internal wall of the blood vessel curved in three-dimensional space. Blood flowing through the three-dimensional curved part of the blood vessel then undergoes a swirling action. The swirling flow of blood has been found to minimise thrombosis and platelet adhesion, and to minimise or prevent coverage of the stent 1 by ingrowth of intima. The flow pattern in the blood vessel including the swirling pattern induced by the non-planar geometry of the blood vessel operates to inhibit the development of vascular diseases such as thrombosis/atherosclerosis and intimal hyperplasia.

The helical shape of the loaded stent 1 ensures that there are no points of high stress in the stent 1.

Figure 3:
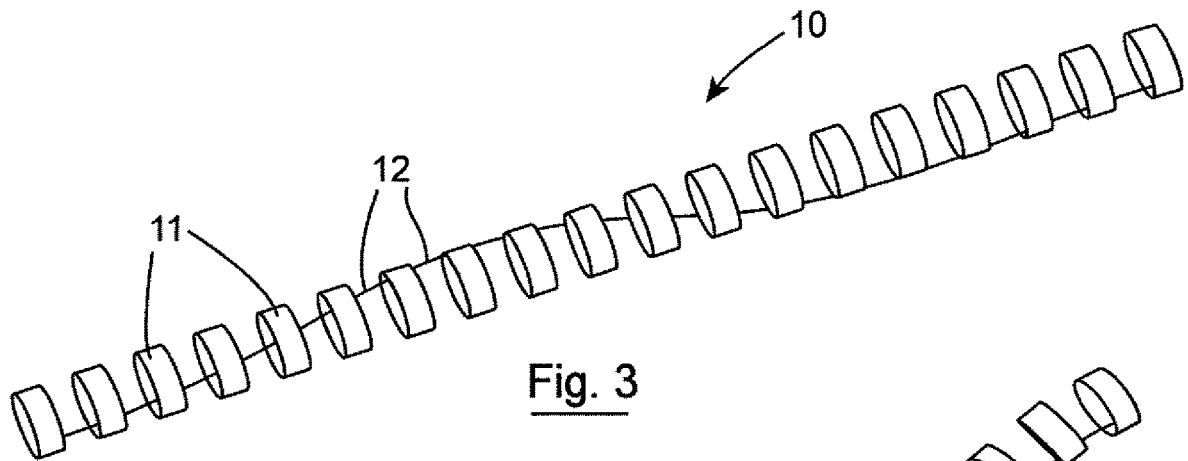
FIG. 3 is an isometric view of another medical device according to the invention in an unloaded configuration.
Figure 4:
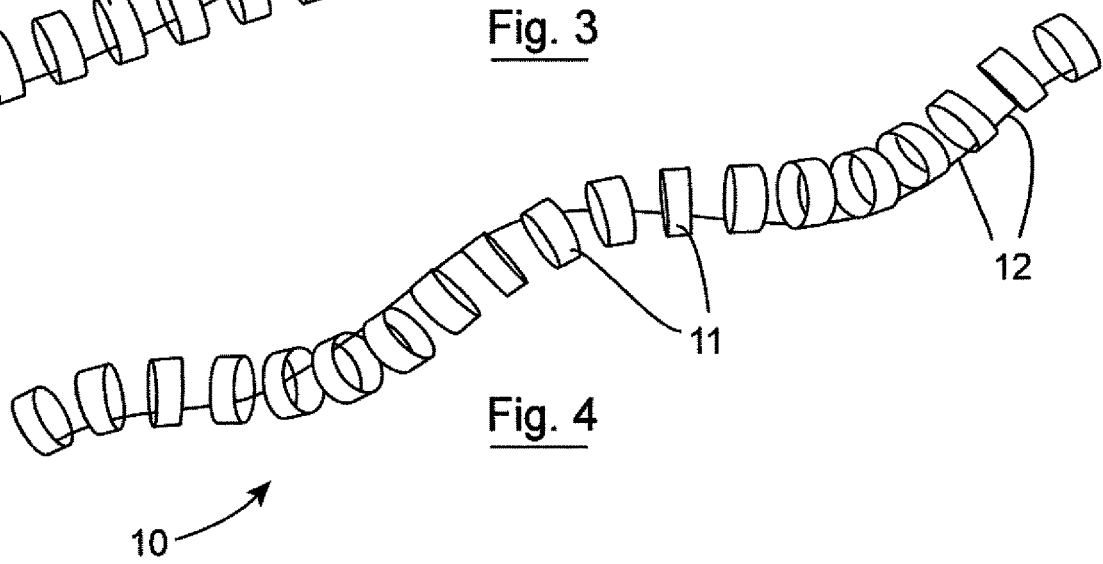
FIG. 4 is an isometric view of the device of FIG. 3 in a loaded configuration.

In FIGS. 3 and 4 there is illustrated another stent 10 according to the invention, which is similar to the stent 1 of FIGS. 1 and 2.

In this case the stent 10 comprises a plurality of longitudinally spaced-apart annular elements 11, and a plurality of primary connecting elements 12 to connect adjacent annular elements 11. A single connecting element 12 connects each annular element 11 to an adjacent annular element 11. The annular elements 11 are shown schematically as solid cylinders but in practice may be made up of struts or the like, or a combination of struts or the like and a covering material, together creating an overall annular shape.

Each primary connecting element 12 is circumferentially offset from the previous primary connecting element 12. In the unloaded configuration (FIG. 3) the longitudinal axis of the aggregation of the plurality of primary connecting elements 12 is curved in three-dimensional space. In this manner the connecting elements 12 snake helically around the stent 10.

In this patent specification the term 'aggregation' will be understood to mean the grouping together of separate elements so that the separate elements may be considered as a whole.

FIGS. 3 and 4 illustrate the stent 10 in which the location of the axial connecting elements 12 which connect the annular elements 11 dictate the loaded, deformed geometry of the stent 10. Since the connecting elements 12 are offset from one another in subsequent annular elements 11, the stent 10 will take up the three dimensional, e.g. helical, centreline curvature upon compressive loading.

Figure 5:
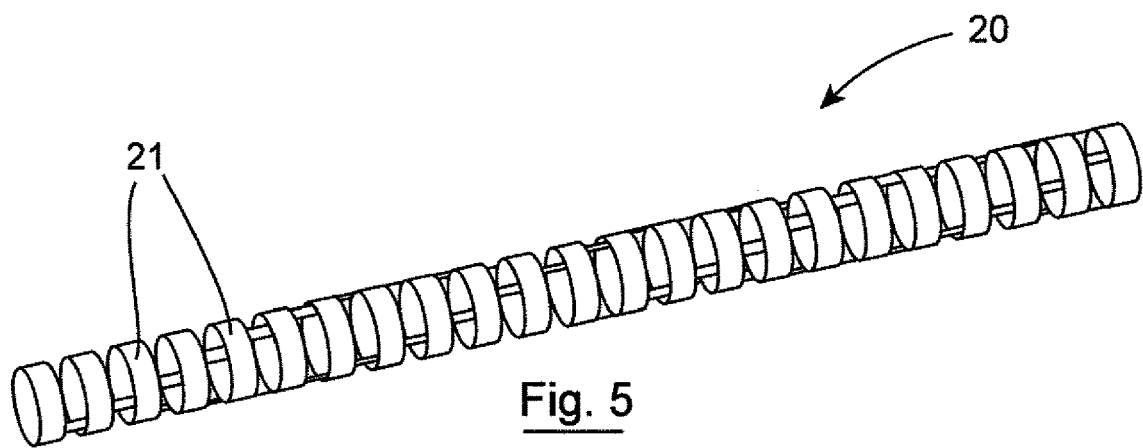
FIG. 5 is an isometric view of another medical device according to the invention in an unloaded configuration.
Figure 6:
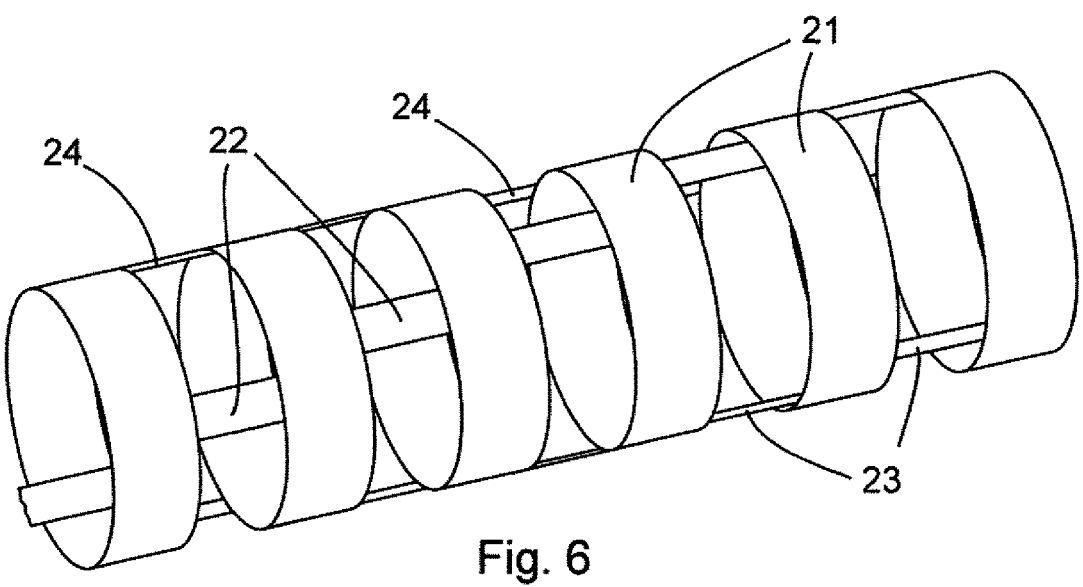
FIG. 6 is an enlarged isometric view of pail of the device of FIG. 5 in the unloaded configuration.
Figure 7:
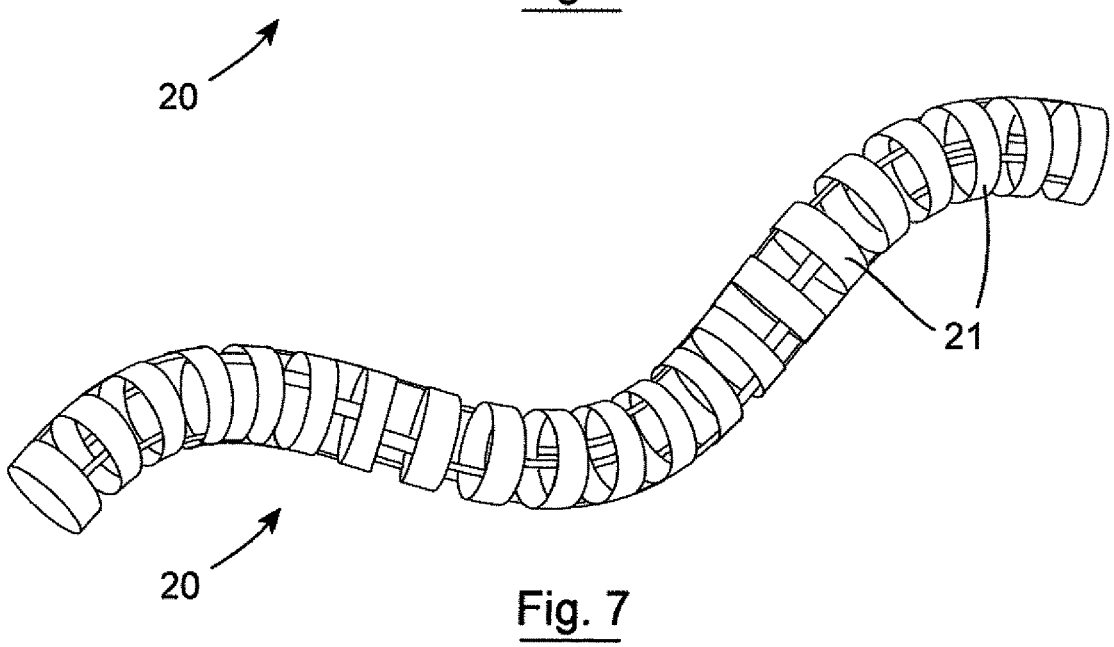
FIG. 7 is an isometric view of the device of FIG. 5 in a loaded configuration.

FIGS. 5 to 7 illustrate a further stent 20 according to the invention, which is similar to the stent 10 of FIGS. 3 and 4.

In this case the stent 20 comprises the plurality of longitudinally spaced-apart annular elements 21, the plurality of primary connecting elements 22 to connect adjacent annular elements 21, a plurality of secondary connecting elements 23 to connect adjacent annular elements 21, and a plurality of tertiary connecting elements 24 to connect adjacent annular elements 21. Three connecting elements 22, 23, 24 connect each annular element 21 to an adjacent annular element 21. The annular elements 21 are shown schematically as solid cylinders but in practice may be made up of struts or the like, or a combination of struts or the like and a covering material, together creating an overall annular shape.

Each primary connecting element 22 is circumferentially offset from the previous primary connecting element 22. In the unloaded configuration (FIGS. 5 and 6) the longitudinal axis of the aggregation of the plurality of primary connecting elements 22 is curved in three-dimensional space. Similarly each secondary connecting element 23 is circumferentially offset from the previous secondary connecting element 23. In the unloaded configuration (FIGS. 5 and 6) the longitudinal axis of the aggregation of the plurality of secondary connecting elements 23 is curved in three-dimensional space. Similarly each tertiary connecting element 24 is circumferentially offset from the previous tertiary connecting element 24. In the unloaded configuration (FIGS. 5 and 6) the longitudinal axis of the aggregation of the plurality of tertiary connecting elements 24 is curved in three-dimensional space.

The circumferential dimension of each primary connecting element 22 is greater than the circumferential dimension of each secondary connecting element 23, and the circumferential dimension of each primary connecting element 22 is greater than the circumferential dimension of each tertiary connecting element 24. In this case the circumferential dimension of each secondary connecting element 23 is equal to the circumferential dimension of each tertiary connecting element 24. The dominant connecting element 22 is of larger dimension than the other connecting elements 23, 24. The dominant connecting element 22 is arranged in the helical snake form.

FIGS. 5 to 7 illustrate the variations in the strut thickness used to achieve the three dimensional curvature during loading. The stent 20 has the struts 22, 23, 24 of differing width between the annular elements 21. The strut width pattern is indexed by an angle between adjacent annular elements 21. Under a compressive load the stent 20 will compress into a helical shape with three dimensional longitudinal centreline curvature.

Figure 8:
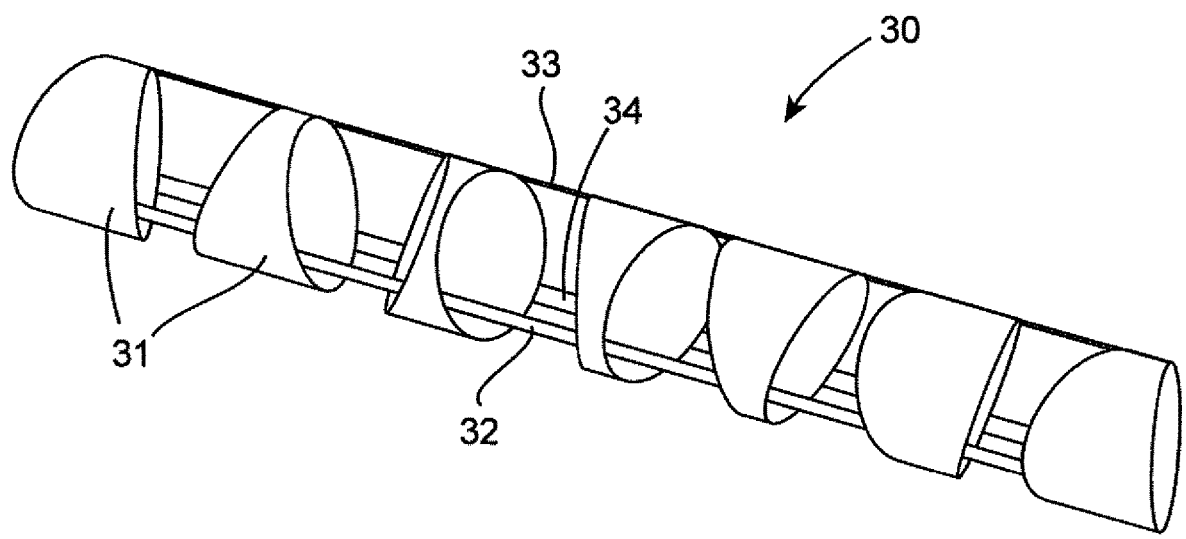
FIG. 8 is an isometric view of another medical device according to the invention in an unloaded configuration.
Figure 9:
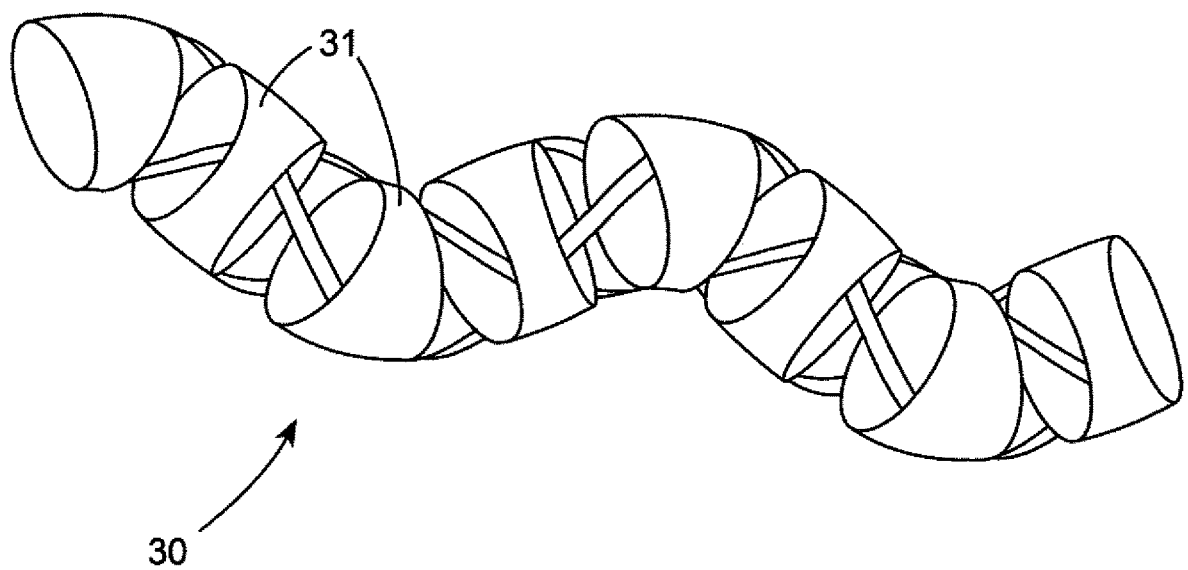
FIG. 9 is an isometric view of the device of FIG. 8 in a loaded configuration.

Referring to FIGS. 8 and 9 there is illustrated another stent 30 according to the invention, which is similar to the stent 20 of FIGS. 5 to 7.

In this case the stent 30 comprises the plurality of longitudinally spaced-apart annular elements 31, the plurality of primary connecting elements 32 to connect adjacent annular elements 31, the plurality of secondary connecting elements 33 to connect adjacent annular elements 31, and the plurality of tertiary connecting elements 34 to connect adjacent annular elements 31. Three connecting elements 32, 33, 34 connect each annular element 31 to an adjacent annular element 31. The annular elements 31 are shown schematically as solid cylinders but in practice may be made up of struts or the like, or a combination of struts or the like and a covering material, together creating an overall annular shape.

The longitudinal dimension of each annular element 31 varies around the circumference of the annular element 31. For each annular element 31 the point on the circumference of the annular element 31 where the longitudinal dimension is at a maximum is circumferentially offset from the point on the circumference of the previous annular element 31 where the longitudinal dimension is at a maximum. In the unloaded configuration (FIG. 8) the longitudinal axis of the aggregation of the points of maximum longitudinal dimension is curved in three-dimensional space, e.g. helical.

Each primary connecting element 32 is circumferentially offset from the previous primary connecting element 32. In the unloaded configuration (FIG. 8) the longitudinal axis of the aggregation of the plurality of primary connecting elements 32 is curved in three-dimensional space, e.g. helical. Similarly each secondary connecting element 33 is circumferentially offset from the previous secondary connecting element 33. In the unloaded configuration (FIG. 8) the longitudinal axis of the aggregation of the plurality of secondary connecting elements 33 is curved in three-dimensional space, e.g. helical. Similarly each tertiary connecting element 34 is circumferentially offset from the previous tertiary connecting element 34. In the unloaded configuration (FIG. 8) the longitudinal axis of the aggregation of the plurality of tertiary connecting elements 34 is curved in three-dimensional space, e.g. helical.

The longitudinal dimension of each primary connecting element 32 is greater than the longitudinal dimension of each secondary connecting element 33, and the longitudinal dimension of each secondary connecting element 33 is greater than the longitudinal dimension of each tertiary connecting element 34.

In FIGS. 8 and 9 each annular element 31 has a variable length. Subsequent annular elements 31 are rotated relative to each other and this results in the connectors 32, 33, 34 between the annular elements 31 having variable lengths. The short side of the annular elements 31 are arranged in a spiral fashion, such that under a compressive load the stent 30 will compress into a helical shape with three dimensional longitudinal centreline curvature.

In FIGS. 10 to 15 there is illustrated another stent 40 according to the invention, which is similar to the stent 1 of FIGS. 1 and 2.

Figure 10:
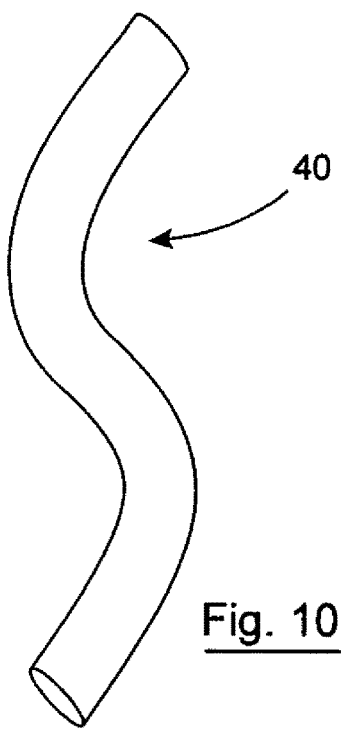
FIG. 10 is an isometric view of another medical device according to the invention in an unloaded configuration.
Figure 11:
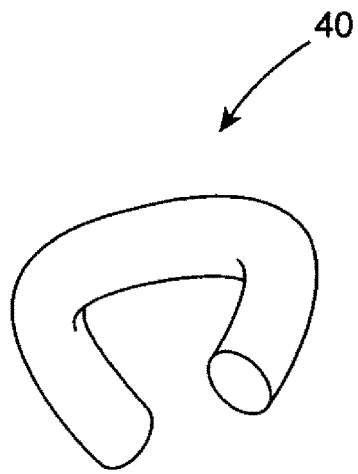
FIG. 11 is an isometric view of the device of FIG. 10 in a loaded configuration.
Figure 12:
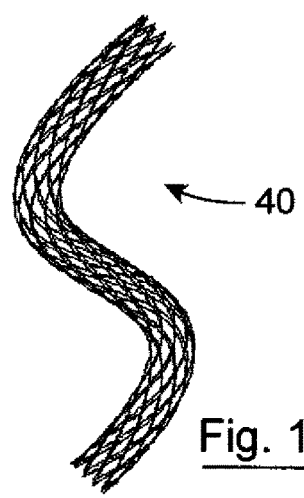
FIG. 12 is a front view of the device of FIG. 10 in the unloaded configuration.
Figure 13:
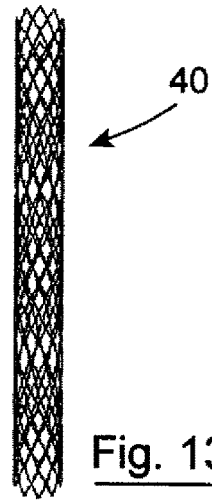
FIG. 13 is an end view of the device of FIG. 10 in the unloaded configuration.
Figure 14:
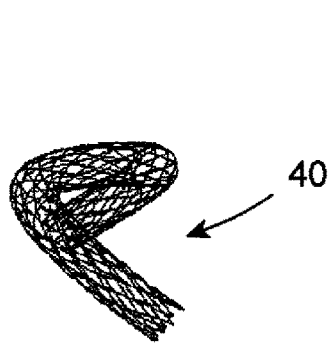
FIG. 14 is a front view of the device of FIG. 10 in the loaded configuration.
Figure 15:
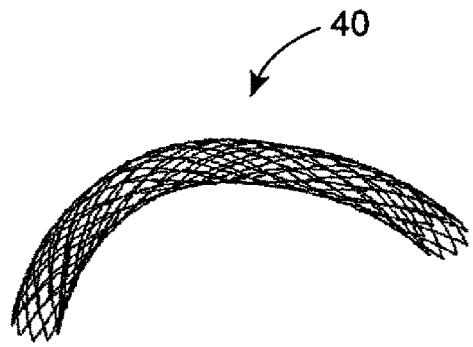
FIG. 15 is an end view of the device of FIG. 10 in the loaded configuration.

In this case the longitudinal axis of the stent 40 is curved in a two-dimensional plane in the unloaded configuration (FIGS. 10, 12, 13).

FIGS. 10 to 15 illustrate the stent 40 with the two-dimensional bend when in the unloaded state. Bending of the stent 40, for example behind the knee, induces the three-dimensional curvature. When implanted at a site subject to bending, for example behind the knee, three dimensional curvature is achieved when the stent 40 bends.

Figure 16:
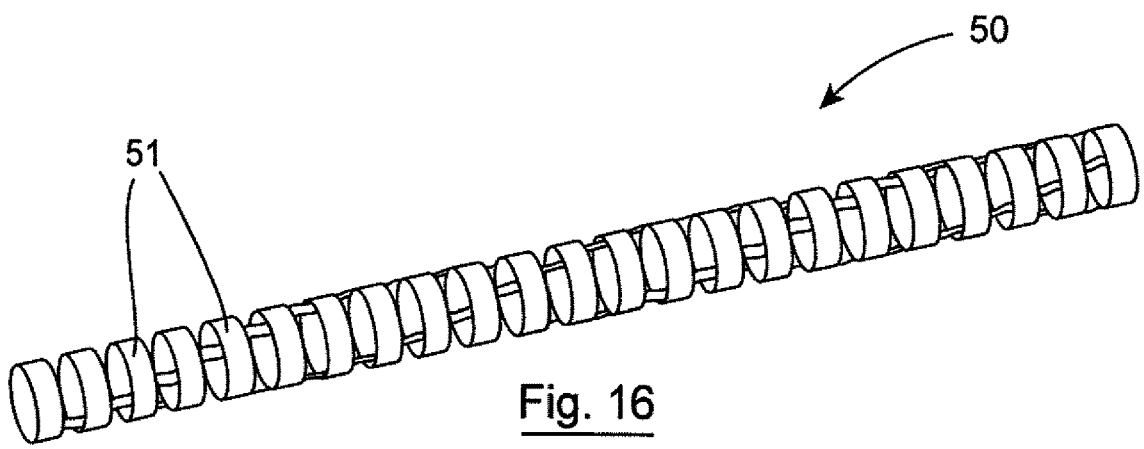
FIG. 16 is an isometric view of another medical device according to the invention in an unloaded configuration.
Figure 17:
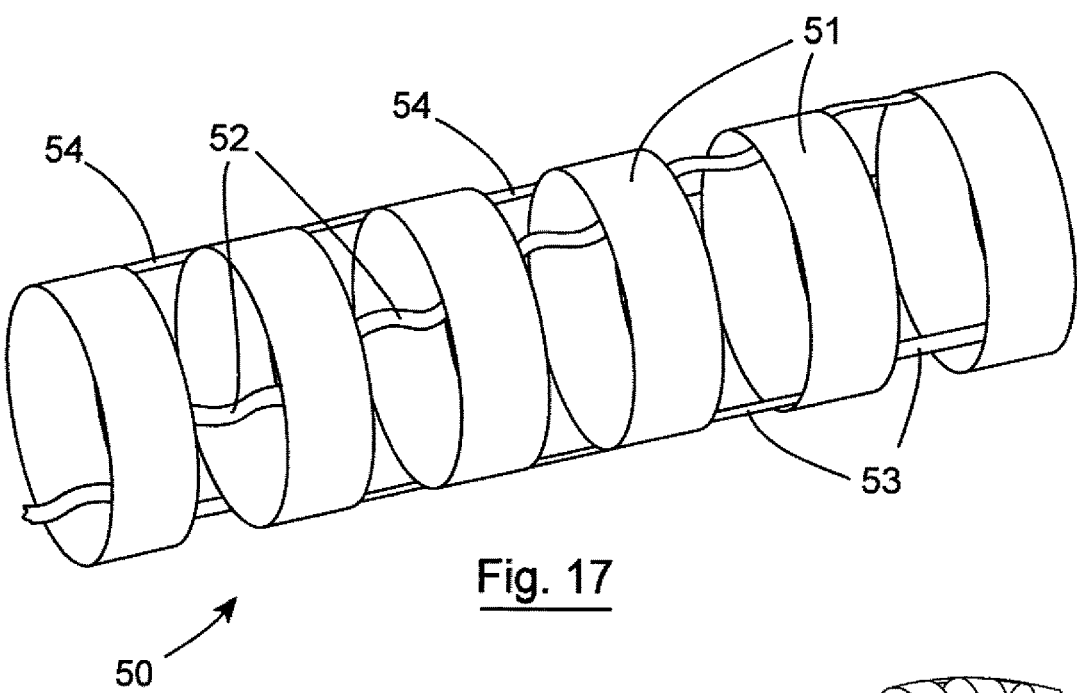
FIG. 17 is an enlarged isometric view of part of the device of FIG. 16 in the unloaded configuration.
Figure 18:
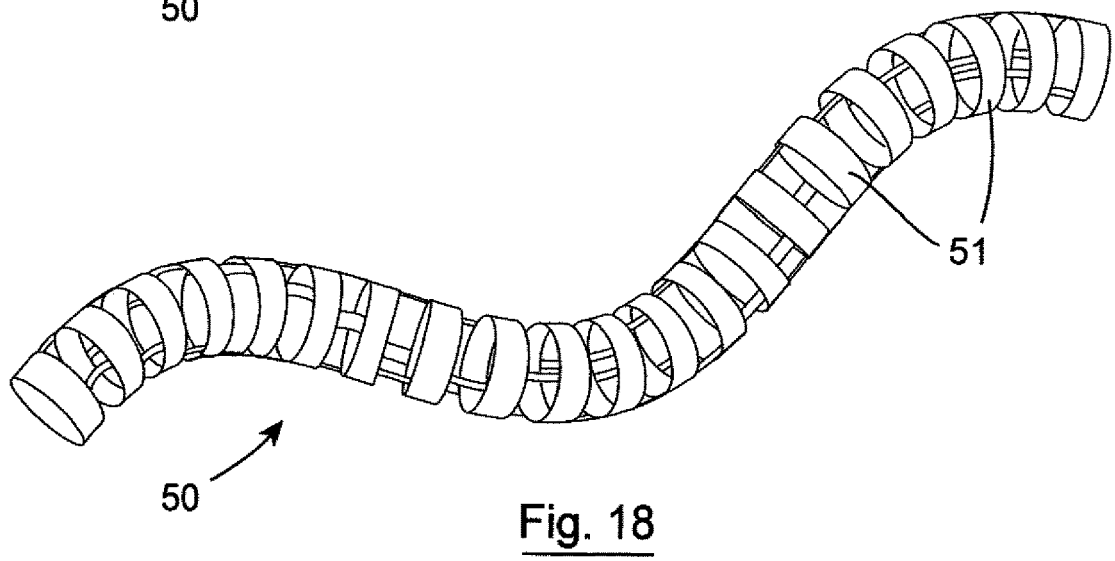
FIG. 18 is an isometric view of the device of FIG. 16 in a loaded configuration.

FIGS. 16 to 18 illustrate a further stent 50 according to the invention, which is similar to the stent 20 of FIGS. 5 to 7.

In this case the stent 50 comprises the plurality of longitudinally spaced-apart annular elements 51, the plurality of primary connecting elements 52 to connect adjacent annular elements 51, the plurality of secondary connecting elements 53 to connect adjacent annular elements 51, and the plurality of tertiary connecting elements 54 to connect adjacent annular elements 51. Three connecting elements 52, 53, 54 connect each annular element 51 to an adjacent annular element 51. The annular elements 51 are shown schematically as solid cylinders but in practice may be made up of struts or the like, or a combination of struts or the like and a covering material, together creating an overall annular shape.

Each primary connecting element 52 is circumferentially offset from the previous primary connecting element 52. In the unloaded configuration (FIGS. 16 and 17) the longitudinal axis of the aggregation of the plurality of primary connecting elements 52 is curved in three-dimensional space, e.g. helical. Similarly each secondary connecting element 53 is circumferentially offset from the previous secondary connecting element 53. In the unloaded configuration (FIGS. 16 and 17) the longitudinal axis of the aggregation of the plurality of secondary connecting elements 53 is curved in three-dimensional space, e.g. helical. Similarly each tertiary connecting element 54 is circumferentially offset from the previous tertiary connecting element 54. In the unloaded configuration (FIGS. 16 and 17) the longitudinal axis of the aggregation of the plurality of tertiary connecting elements 54 is curved in three-dimensional space, e.g. helical.

The circumferential dimension of each primary connecting element 52 is equal to the circumferential dimension of each secondary connecting element 53, and the circumferential dimension of each primary connecting element 52 is equal to the circumferential dimension of each tertiary connecting element 54.

Each primary connecting element 52 extends in a curve between adjacent annular elements 51 to form a point of weakness in the primary connecting element 52. Each secondary connecting element 53 and each tertiary connecting element 54 extends in a straight manner between adjacent annular elements 51. In this manner the stiffness of each primary connecting element 52 is less than the stiffness of each secondary connecting element 53, and the stiffness of each primary connecting element 52 is less than the stiffness of each tertiary connecting element 54. Under a compressive load the stent 50 will compress into a helical shape with three dimensional longitudinal centreline curvature.

It will be appreciated that the three-dimensional curved shape of the stent in the loaded configuration may be achieved using a variety of possible means.

The radial dimension of the primary connecting element may be greater than the radial dimension of the secondary connecting element.

The three dimensional curvature may be achieved by varying the width and/or thickness of the axial connecting elements between adjacent annular elements.

The stent may include a point of weakness. The point of weakness may be arranged in the helical snake form.

The number of connecting elements may be varied, the geometry of the annular elements may be varied, the overall stent pattern may be varied.

Regional variations in the properties of the stent may be achieved by varying the materials used to construct the stent.

Any combination of the means disclosed may be used to achieve the desired regional variations in the stent properties, which leads to the three dimensional curvature during loading.

It will also be appreciated that the stent may be of any suitable construction, for example the stent may be of braided construction, the stent may be cut from a tube as a self expanding or balloon expandable stent, the stent may comprise elements connected using welds. Each annular element may be in the form of a crown or alternatively may be in the form of a cuff which extends circumferentially in a hoop.

It will further be appreciated that although compression is given as an example of loading, the stent may achieve the three dimensional curvature under other loading modes depending on the regional property variations in the stent.

It will also be appreciated that the medical device of the invention is suitable for location in a variety of types of blood vessel, for example the medical device may be employed in a coronary application.

The invention is not limited to the embodiments hereinbefore described, with reference to the accompanying drawings, which may be varied in construction and detail.

The invention claimed is:

1. A medical device suitable for location in a body lumen, wherein upon application of a load to the device the device is movable from an unloaded configuration to a loaded configuration, wherein in the unloaded configuration at least part of a longitudinal axis of the device is curved in a two-dimensional plane; wherein in the loaded configuration at least part of the longitudinal axis of the device is curved in three-dimensional space; the device being biased to achieve the three-dimensional curvature during loading;
   wherein the device comprises:
      a plurality of annular elements and a plurality of primary connecting elements to connect adjacent annular elements, and
      a plurality of secondary connecting elements to connect adjacent annular elements.

2. A device as claimed in claim 1, wherein in the loaded configuration at least part of the device is substantially helically shaped.

3. A device as claimed in claim 1, wherein in the loaded configuration at least part of the device is substantially spiral shaped.

4. A device as claimed in claim 1, wherein the device is configured to move from the unloaded configuration to the loaded configuration upon application of a compressive load to the device.

5. A device as claimed in claim 1, wherein the device comprises a first secondary connecting element to connect a first annular element to a second annular element, and a second secondary connecting element to connect the second annular element to a third annular element, the first secondary connecting element being circumferentially offset from the second secondary connecting element.

6. A device as claimed in claim 1, wherein an aggregation of secondary connecting elements comprises a grouping of said plurality of secondary connecting elements considered together as a whole, and wherein in the unloaded configuration at least part of a longitudinal axis of the aggregation of the plurality of secondary connecting elements is curved in three-dimensional space.

7. A device as claimed in claim 1, wherein a circumferential dimension of each of the plurality of primary connecting elements is greater than a circumferential dimension of each of the plurality of secondary connecting elements.

8. A device as claimed in claim 1, wherein a longitudinal dimension of each of the plurality of primary connecting elements is greater than a longitudinal dimension of each of the plurality of secondary connecting elements.

9. A device as claimed in claim 1, wherein a radial dimension of each of the plurality of primary connecting elements is greater than a radial dimension of each of the plurality of secondary connecting elements.

10. A device as claimed in claim 1, wherein a stiffness of each of the plurality of primary connecting elements is less than a stiffness of each of the plurality of secondary connecting elements.

11. A device as claimed in claim 1, wherein a longitudinal dimension of each of the plurality of annular elements varies around a circumference of the annular element.

12. A device as claimed in claim 11, wherein the plurality of annular elements comprises a first annular element and a second annular element, a point on the circumference of the first annular element where the longitudinal dimension is at a maximum being circumferentially offset from a point on the circumference of the second annular element where the longitudinal dimension is at a maximum.

13. A device as claimed in claim 11, wherein in the unloaded configuration at least part of a longitudinal axis of an aggregation of a plurality of points on the circumference of the plurality of annular elements where the longitudinal dimension is at a maximum is curved in three-dimensional space.

14. A device as claimed in claim 1, wherein the device comprises a stent suitable for deployment in a blood vessel.

15. A device as claimed in claim 1, wherein the device is expandable from a delivery configuration to an expanded deployed configuration, and wherein said application of a load to the device is configured to occur when the device is in the expanded deployed configuration, and wherein said unloaded configuration from which the device is movable is an unloaded expanded deployed configuration and said loaded configuration to which the device is movable is a loaded expanded deployed configuration.

16. A device as claimed in claim 1, wherein in the loaded configuration the device is configured to cause at least part of a longitudinal axis of the body lumen in which it is deployed to curve in three-dimensional space.

17. A device as claimed in claim 1, wherein the device has properties with regional variations, the regional variations biasing the device to achieve the three-dimensional curvature during loading.

18. A medical device suitable for location in a body lumen, wherein upon application of a load to the device, the device is movable from an unloaded configuration to a loaded configuration, wherein in the unloaded configuration at least part of a longitudinal axis of the device is curved in a two-dimensional plane, wherein in the loaded configuration at least part of the longitudinal axis of the device is curved in three-dimensional space, the device being biased to achieve the three-dimensional curvature during loading, the device comprising a plurality of annular elements and a plurality of primary connecting elements to connect adjacent annular elements;
wherein:
a first of the primary connecting elements connects a first of the annular elements to a second of the annular elements and a second of the primary connecting elements connecting the second annular element to a third annular element, the first primary connecting element being circumferentially offset from the second primary connecting element, and/or
an aggregation of primary connecting elements comprises a grouping of the primary connecting elements considered together as a whole and, in the unloaded configuration, at least part of a longitudinal axis of the aggregation of the primary connecting elements is curved in three-dimensional space.

19. A device as claimed in claim 18, wherein:
in the loaded configuration, at least part of the device is substantially helically shaped; and/or
the device is configured to move from the unloaded configuration to the loaded configuration upon application of a compressive load to the device.

20. A device as claimed in claim 18, wherein in the loaded configuration, the device is configured to cause at least part of a longitudinal axis of the body lumen in which it is deployed to curve in three-dimensional space.

21. A medical device suitable for location in a body lumen, wherein upon application of a load to the device, the device is movable from an unloaded configuration to a loaded configuration,
wherein in the unloaded configuration, at least part of a longitudinal axis of the device is curved in a two-dimensional plane;
wherein in the loaded configuration, at least part of the longitudinal axis of the device is curved in three-dimensional space, the device being biased to achieve the three-dimensional curvature during loading;
wherein the device has properties with regional variations, the regional variations biasing the device to achieve the three-dimensional curvature during loading.

22. A device as claimed in claim 21, wherein:
in the loaded configuration, at least part of the device is substantially helically shaped; and/or
the device is configured to move from the unloaded configuration to the loaded configuration upon application of a compressive load to the device.

23. A device as claimed in claim 21, wherein in the loaded configuration the device is configured to cause at least part of a longitudinal axis of the body lumen in which it is deployed to curve in three-dimensional space.

24. A medical device suitable for location in a body lumen, wherein upon application of a load to the device, the device is movable from an unloaded configuration to a loaded configuration,
wherein in the unloaded configuration, at least part of a longitudinal axis of the device is curved in a two-dimensional plane;
wherein in the loaded configuration, at least part of the longitudinal axis of the device is curved in three-dimensional space, the device being biased to achieve the three-dimensional curvature during loading;

wherein the device comprises a plurality of annular elements;

and wherein a longitudinal dimension of each of the plurality of annular elements varies around a circumference of the annular element.

25. A device as claimed in claim 24, wherein:

in the loaded configuration, at least part of the device is substantially helically shaped; and/or the device is configured to move from the unloaded configuration to the loaded configuration upon application of a compressive load to the device.

26. A device as claimed in claim 24, wherein in the loaded configuration the device is configured to cause at least part of a longitudinal axis of the body lumen in which it is deployed to curve in three-dimensional space.

27. A device as claimed in claim 24, wherein:

the plurality of annular elements comprises a first annular element and a second annular element, a point on the circumference of the first annular element where the longitudinal dimension is at a maximum being circumferentially offset from a point on the circumference of the second annular element where the longitudinal dimension is at a maximum; and/or in the unloaded configuration at least part of a longitudinal axis of an aggregation of a plurality of points on the circumference of the plurality of annular elements where the longitudinal dimension is at a maximum is curved in three-dimensional space.

* * * * *